US005728529A

United States Patent [19]

Metzker et al.

[11] Patent Number: 5,728,529

[45] Date of Patent: Mar. 17, 1998

[54] ALTERNATIVE DYE-LABELED RIBONUCLEOTIDES, DEOXYRIBONUCLEOTIDES, AND DIDEOXYRIBONUCLEOTIDES FOR AUTOMATED DNA ANALYSIS

[75] Inventors: Michael L. Metzker; Richard A. Gibbs, both of Houston, Tex.

[73] Assignee: Baylor College Of Medicine, Houston, Tex.

[21] Appl. No.: 553,936

[22] Filed: Nov. 6, 1995

Related U.S. Application Data

[63] Continuation-in-part of Ser. No. 494,216, Jun. 23, 1995, Pat. No. 5,614,386.

[51] Int. Cl.$^6$ .............................. C12Q 1/68; C12Q 1/70; C07H 21/04; C12P 19/34
[52] U.S. Cl. .............................. 435/6; 435/5; 435/91.1; 435/91.2; 536/24.3; 536/24.32; 536/24.33; 422/82.07; 422/82.08; 548/405
[58] Field of Search ........................ 435/6, 5, 91.1, 435/91.2; 536/24.3, 25.32; 422/82.07, 82.08; 548/405; 252/700

[56] References Cited

U.S. PATENT DOCUMENTS

| | | |
|---|---|---|
| 4,318,846 | 3/1982 | Khanna . |
| 4,744,339 | 5/1988 | Haughland et al. . |
| 4,755,458 | 7/1988 | Rabbani . |
| 4,811,218 | 3/1989 | Hunkapiller et al. . |
| 4,855,225 | 8/1989 | Fung et al. . |
| 5,151,507 | 9/1992 | Hobbs . |
| 5,171,534 | 12/1992 | Smith et al. . |
| 5,188,934 | 2/1993 | Menchen et al. . |
| 5,241,060 | 8/1993 | Englehardt . |
| 5,274,113 | 12/1993 | Kang et al. . |
| 5,366,603 | 11/1994 | Middendorf et al. . |
| 5,366,860 | 11/1994 | Bergot et al. . |
| 5,433,896 | 7/1995 | Kang et al. . |

FOREIGN PATENT DOCUMENTS

| | | |
|---|---|---|
| 0025912 | 4/1981 | European Pat. Off. . |
| 0233053 | 8/1987 | European Pat. Off. ...... C07D 311/82 |
| WO91/0506 | 4/1991 | WIPO . |

OTHER PUBLICATIONS

Haugland et al. Report from Energy Abstracts 17(6) Abstr No. 16972, 1992.
Metzker et al., Termination of DNA synthesis by novel 3'-modified-deoxyribonucleoside 5'-triphosphates, *Nucleic Acids Research*, 22:4259–4267 (1994).
Drmanac et al., Sequencing of Megabase Plus DNA by Hybridization: Theory of the Method; *Genomics*, 4:114–28 (1989).
Khrapko et al., An oligonucleotide hybridization approach to DNA sequencing, *FEB*, 256:118–22 (1989).
Strezoska et al., DNA sequencing by hybridization: 100 bases read by a non-gel-based method; *PNAS*, 88:10089–93 (1991).

Boude et al., Enhanced DNA sequencing by hybridization; *PNAS*, 91:3072–76 (1994).
Pease et al., Light-generated oligonucleotide arrays for rapid DNA sequence analysis; *PNAS*, 91:5022–26 (1994).
Studier, A strategy for high-volume sequencing of cosmid DNAs: Random and directed priming with a library of oligonucleotides; *PNAS*, 86:6917–21 (1989).
Kieleczawa et al., DNA Sequencing by Primer Walking with Strings of Contiguous Hexamers; *Science*, 258:1787–91 (1992).
Swerdlow et al., Capillary gel electrophoresis for rapid, high resolution DNA sequencing; *Nucleic Acids Research*, 18:1415–19 (1990).
Karger et al., Multiwavelength fluorescence detection for DNA sequencing using capillary electrophoresis, *Nucleic Acids Research*, 19:4955–62 (1991).
Ruiz–Martinez et al., DNA Sequencing by Capillary Electrophoresis with Replaceable Linear Polyacrylamide and Laser–Inducted Fluorescence Detection; *Anal Chem.*, 65:2851–58.
Prober et al., A System for Rapid DNA Sequencing with Fluorescent Chain–Terminating Dideoxynucleotides, *Science*, 238:336–41 (1987).
Smith et al., Fluorescence detection in automated DNA sequence analysis; *Nature*, 321:674–79 (1986).
Perkin Elmer advertisement (1994).
Lee, DNA sequencing with dye–labeled terminators and T7DNA polymerase: effect of cyes and dNTPs on incorporation of dye terminators and probability analysis of termination fragments; *Nucleic Acids Research*, 20:2471–83 (1992).
Eggers et al., A Microchip for Quantitative Detection of Molecules Utilizing Luminescent and Radioisotopic Reporter Groups, *BioTechniques*, 17:516–22 (1994).
Khrapko et al., A method for DNA sequencing by hybridization with oligonucleotide matrix, *J. DNA Sequencing and Mapping* 1:375–88 (1991).

*Primary Examiner*—W. Gary Jones
*Assistant Examiner*—Dianne Rees
*Attorney, Agent, or Firm*—Fulbright & Jaworski L.L.P.

[57] ABSTRACT

Methods for the use of a class of dyes for improved DNA sequencing by the chain termination method of DNA sequencing, and internal labelling of polynucleotides by enzymatic incorporation of fluorescently-labeled ribonucleotides or deoxyribonucleotides are provided. A new class of dyes, BODIPY® fluorophores, has been described recently. The parent heterocyclic molecule of the BODIPY® fluorophores is a dipyrromethaneboron difluoride compound which is modified to create a broad class of spectrally-discriminating fluorophores. BODIPY® fluorophores have improved spectral characteristics compared to conventional fluorescein and rhodamine dyes. BODIPY® fluorophores have narrower band width, insensitivity to solvent or pH, and improved photostability, thus, BODIPY® fluorophores lead to improved DNA sequencing and/or detection in any method where electrophoresis and detection of DNA is required. Additionally, the spectral properties of the BODIPY® fluorophores are sufficiently similar in wavelength and intensity to be used with conventional equipment known in the art.

17 Claims, 2 Drawing Sheets

FIG. 1

BODIPY 503/512

BODIPY 530/550

BODIPY 558/568

BODIPY 564/570

BODIPY 576/589

BODIPY 589/616

BODIPY 581/591

FIG. 2

ALTERNATIVE DYE-LABELED RIBONUCLEOTIDES, DEOXYRIBONUCLEOTIDES, AND DIDEOXYRIBONUCLEOTIDES FOR AUTOMATED DNA ANALYSIS

REFERENCE TO PRIOR APPLICATIONS

The present application is a Continuation-in-part of U.S. Ser. No. 08/494,216, filed Jun. 23, 1995 now U.S. Pat. No. 5,614,386.

This invention was supported in part by a grant from the United States Government through the National Institutes of Health (Grant Nos. P30HG00210 (NIH) and T32HG00003 (NIH-NCHGR). The U.S. Government has certain rights in this invention.

FIELD OF THE INVENTION

This invention relates generally to methods for the use of a class of dyes for improved DNA sequencing by the chain termination method of DNA sequencing and for internal labelling of polynucleotides by enzymatic incorporation of fluorescently-labeled ribonucleotides or deoxyribonucleotides.

BACKGROUND

The present invention relates to methods for the use of a new class of dyes for DNA sequencing by the chain termination method of DNA sequencing and for internal labelling of polynucleotides by enzymatic incorporation of fluorescently-labeled ribonucleotides or deoxyribonucleotides. The ability to determine the sequence of DNA is critical for understanding the function and control of genes and for applying many of the basic techniques of molecular biology. Native DNA consists of two linear polymers, or strands, of nucleotides. Each strand is a chain of nucleosides linked by phosphodiester bonds. The two strands are held together in an antiparallel orientation by hydrogen bonds between complementary bases of the nucleotides of the two strands: deoxyadenosine triphosphate (A) pairs with thymidine triphosphate (T) and deoxyguanosine triphosphate (G) pairs with deoxycytidine triphosphate (C).

The development of reliable methods for sequence analysis of DNA (deoxyribonucleic acid) and RNA (ribonucleic acid) has been essential to the success of recombinant DNA and genetic engineering. When used with the other techniques of modern molecular biology, nucleic acid sequencing allows dissection of animal, plant and viral genomes into discrete genes with defined chemical structure. Since the function of a biological molecule is determined by its structure, defining the structure of a gene is crucial to the eventual useful manipulation of this basic unit of hereditary information. Once genes can be isolated and characterized, they can be modified to produce desired changes in their structure that allow the production of gene products—proteins—with different properties than those possessed by the original gene products.

The development of modern nucleic acid sequencing methods involved parallel developments in a variety of techniques. One was the emergence of simple and reliable methods for cloning small to medium-sized strands of DNA into bacterial plasmids, bacteriophages, and small animal viruses. Cloning allowed the production of pure DNA in sufficient quantities to allow chemical analysis. Another was the use of gel electrophoretic methods for high resolution separation of oligonucleotides on the basis of size. The key development, however, was the introduction of methods of generating sets of fragments of cloned, purified DNA that contain, in their collection of lengths, the information necessary to define the sequence of the nucleotides comprising the parent DNA molecules.

Presently there are several approaches to DNA sequence determination, see, e.g., the dideoxy chain termination method, Sanger et al., *Proc. Natl. Acad. Sci.*, 74:5463–67 (1977); the chemical degradation method, Maxam et al., *Proc. Natl. Acad. Sci.*, 74:560–564 (1977); and hybridization methods, Drmanac et al., *Genomics*, 4:114–28 (1989), Khrapko, *FEB* 256:118–22 (1989). The chain termination method has been improved in several ways, and serves as the basis for all currently available automated DNA sequencing machines. See, e.g., Sanger et al., *J. Mol. Biol.*, 143:161–78 (1980); Schreier et al., *J. Mol. Biol.*, 129:169–72 (1979); Smith et al., *Nucleic Acids Research*, 13:2399–2412 (1985); Smith et al., *Nature*, 321:674–79 (1987) and U.S. Pat. No. 5,171,534; Prober et al., *Science*, 238:336–41 (1987); Section II, *Meth. Enzymol.*, 155:51–334 (1987); Church et al., *Science*, 240:185–88 (1988); Swerdlow and Gesteland, *Nucleic Acids Research*, 18:1415–19 (1989); Ruiz-Martinez et al., *Anal. Chem.*, 2851–58 (1993); Studier, *PNAS*, 86:6917–21 (1989); Kieleczawa et al., *Science*, 258:1787–91; and Connell et al., *Biotechniques*, 5:342–348 (1987).

The method developed by Sanger is referred to as the dideoxy chain termination method. In a commonly-used variation of this method, a DNA segment is cloned into a single-stranded DNA phage such as M13. These phage DNAs can serve as templates for the primed synthesis of the complementary strand by conventional DNA polymerases. The primer is either a synthetic oligonucleotide or a restriction fragment isolated from the parental recombinant DNA that hybridizes specifically to a region of the M13 vector near the 3' end of the cloned insert. In each of four sequencing reactions, the primed synthesis is carried out in the presence of enough of the dideoxy analog of one of the four possible deoxynucleotides so that the growing chains are randomly terminated by the incorporation of these "deadend" nucleotides. The relative concentration of dideoxy to deoxy forms is adjusted to give a spread of termination events corresponding to all the possible chain lengths that can be resolved by gel electrophoresis. The products from each of the four primed synthesis reactions are loaded into individual lanes and are separated by polyacrylamide gel electrophoresis. Radioactive label incorporated in the growing chains are used to develop an autoradiogram image of the pattern of the DNA in each electrophoresis lane. The sequence of the deoxynucleotides in the cloned DNA is determined from an examination of the pattern of bands in the four lanes. Because the products from each of the four synthesis reactions must be run on separate gel lanes, there are problems with comparing band mobilities in the different lanes.

Turning to automated DNA sequencing machines, in general, fragments having different terminating bases can be labeled with different fluorescent dyes, which are attached either to a primer, e.g., Smith et al. (1987, cited above), or to the base of a terminal dideoxyribonucleotide, e.g., Prober et al. (cited above). A fluorescence detector then can be used to detect the fluorophore-labeled DNA fragments. The four different dideoxy-terminated samples can be run in four separate lanes or, if labeled differentially, in the same lane. The method of Fung, et al., U.S. Pat. No. 4,855,225, uses a set of four chromophores or fluorophores with different absorption of fluorescent maxima. Each of these tags is coupled chemically to the primer used to initiate the synthesis of the fragment strands. In turn, each tagged primer is then paired with one of the dideoxyribonucleotides and used in the primed synthesis reaction with conventional DNA polymerases. The labeled fragments are then combined and loaded onto the same gel column for electrophoretic separation. Base sequence is determined by analyzing the fluorescent signals emitted by the fragments as they pass a stationary detector during the separation process.

Obtaining a set of dyes to label the different fragments is a major difficulty in automated DNA sequencing systems. First, it is difficult to find three or more dyes that do not have emission bands which overlap significantly since the typical emission band halfwidth for organic fluorescent dyes is about 40–80 nanometers (nm) and the width of the visible spectrum is only about 350–400 nm. Second, even if dyes with non-overlapping emission bands are found, the set may still be unsuitable for DNA sequencing if the respective fluorescent efficiencies are too low. For example, Pringle et al., DNA Core Facilities Newsletter, 1:15–21 (1988), present data indicating that increased gel loading cannot compensate low fluorescent efficiencies.

Another difficulty with obtaining an appropriate set of dyes is that when several fluorescent dyes are used concurrently, excitation becomes difficult because the absorption bands of the dyes are often widely separated. The most efficient excitation occurs when each dye is illuminated at the wavelength corresponding to its absorption band maximum. Thus, one often is forced to compromise between the sensitivity of the detection system and the increased cost of providing separate excitation sources for each dye. In addition, when the number of differently sized fragments in a single column of a gel is greater than a few hundred, the physiochemical properties of the dyes and the means by which they are linked to the fragments become critical because the charge, molecular weight, and conformation of the dyes and linkers must not effect adversely the electrophoretic mobilities of closely-sized fragments. Changes in electrophoretic mobility can result in extensive band broadening or reversal of band positions on the gel, thereby destroying the correspondence between the order of bands and the order of the bases in the nucleic acid sequence. Due to the many problems associated with altered electrophoretic mobility, correction of mobility discrepancies by computer software is necessary in prior art systems. Finally, the fluorescent dyes must be compatible with the chemistry used to create or manipulate the fragments. For example, in the chain termination method the dyes used to label primers and/or the dideoxy chain terminators must not interfere with the activity of the polymerase or reverse transcriptase employed.

Because of these severe constraints only a few sets of fluorescent dyes have been found that can be used in DNA sequencing, particularly automated DNA sequencing, and in other diagnostic and analytical techniques, e.g., Smith et al. (1985, cited above); Prober et al. (cited above); Hood et al., European patent application 8500960; Bergot et al. (cited above); Fung et al. (cited above); Connell et al. (cited above); and Menchen et al., U.S. Pat. No. 5,188,934.

In view of the above, DNA sequencing would be advanced significantly by the availability of new sets of fluorescent dyes which (1) are physiochemically similar, (2) permit detection of spatially overlapping target substances, such as closely spaced bands of DNA on a gel, (3) extend the number of bases that can be determined on a single gel column by current methods of automated DNA sequencing, (4) are amenable for use with a wide range of preparative and manipulative techniques, and (5) otherwise satisfy the numerous requirements listed above. See, Bergot, et al. (cited above).

Until the present invention, one problem encountered was that each fluorophore altered the "normal" electrophoretic mobility of the corresponding termination products during gel electrophoresis such that software correction files were needed to generate accurate, evenly-spaced DNA sequences. See, Smith et al., Nature, 321:674–79 (1986) and U.S. Pat. No. 5,171,534. Thus, the set of discriminating fluorophores described in the literature is small, and the search for improved, alternative dyes has been difficult at best.

There are several different chemical modifications that have been attempted to correct for differences in gel mobility between different dye-labeled primers in automated DNA sequencing. Generally, fluorescein and its derivative dyes labeled in DNA sequencing reactions have different gel mobilities in comparison to rhodamine and its derivative dyes labeled in DNA sequencing reactions. Fluorescein and its derivative dye-labeled reactions typically move through the gel faster (sometimes greater than one base position) than rhodamine and its derivative dye-labeled reactions. For example, if using the −21M13 universal sequencing primer, each fluorophore is coupled to the primer via different linker arm lengths. Both fluoresceins are coupled to the primer using a two-carbon amino linker arm while both rhodamines are coupled to the primer using six-carbon amino linker arm. Mobility correction software, however, is required additionally to generate properly spaced DNA termination fragments. Another example involves custom sequencing primers. These primers refer to any oligonucleotide sequence that can act as a suitable DNA sequencing primer. To all custom sequencing primers, a 5'-leader sequence (5'-CAGGA) must be coupled to the primer and custom sequencing primers must use the M13RP1 mobility correction software to generate properly-spaced DNA termination fragments. The leader sequence is the first five bases of the reverse M13RP1 sequencing primer. M13RP1 is the mobility software file used to generate properly spaced DNA termination fragments for the reverse sequencing primer.

A new class of dyes, BODIPY® (dipyrrometheneboron difluoride) fluorophores, has been recently described. See, Haugland, et al., *Molecular Probes: Handbook of Fluorescent Probes and Research Chemicals*, pp. 24–32, and U.S. Pat. No. 4,774,339. The parent heterocyclic molecule of the BODIPY® fluorophores is a dipyrrometheneboron difluoride compound and which is modified to create a broad class of spectrally-discriminating fluorophores, see FIG. 1. The conventional naming of these dyes is BODIPY® followed by their approximate absorption/emission maxima, i.e., BODIPY® 530/550.

In addition to the specifically cited references above, additional prior art techniques include the following:

U.S. Pat. No. 4,318,846 to Khanna et al. is drawn to diether symmetrically-substituted fluoresceins having at least one anionic group and a linking functionality. Depending on the site of substitution, the compounds can be used as fluorescers absorbing at wavelengths in excess of 500 nm. The compounds can be used as labels in fluorescent immunoassays.

U.S. Pat. No. 4,811,218 to Hunkapiller et al. is drawn to a real-time, automated nucleic acid sequencing apparatus which permits more than one clone to be sequenced at the same time.

U.S. Pat. No. 4,855,225 to Fung et al., is drawn to a method for detecting up to four sets of oligonucleotides that have been differentially-labeled with fluorophores, two of the sets with substituted fluoresceins and two sets with substituted rhodamines, and separated by gel electrophoresis.

U.S. Pat. No. 5,366,860 to Bergot et al., is drawn to a method for detecting up to four sets of oligonucleotides that have been differentially-labeled with fluorophores, all rhodamines with different substitutions, and separated by gel electrophoresis.

U.S. Pat. No. 5,188,934 to Menchen, et al., is drawn to a method for detecting up to four sets of oligonucleotides that have been differentially-labeled with fluorophores, all fluoresceins with different substitutions, and separated by gel electrophoresis.

U.S. Pat. No. 5,171,534 to Smith et al. describes a system for the electrophoretic analysis of DNA fragments produced in DNA sequencing operations. The system comprises a source of chromophore or fluorescent tagged DNA fragments, a zone for contacting an electrophoresis gel, means for introducing said tagged DNA fragments to said zone and photometric means for monitoring the tagged DNA fragments as they move through the gel.

U.S. Pat. No. 5,366,603 is drawn to automatic DNA sequencing wherein the DNA is marked with near infrared fluorescent dyes.

U.S. Pat. No. 5,274,113 to Kang, et al., is drawn to derivatives of dipyrromethenboron difluoride fluorescent dyes that can be attached to nucleic acids, proteins, carbohydrates and other biologically-derived materials. The compounds of Kang, et al., show various functional groups for attachment of the dipyrromethenboron difluoride fluorescent dyes to the biologically-derived materials.

SUMMARY OF THE INVENTION

BODIPY® fluorophores have improved spectral characteristics compared to conventional fluorescein and rhodamine dyes. The BODIPY® fluorophores have narrower band width, insensitivity to solvent or pH, and improved photostability. Thus, the use of BODIPY® fluorophores lead to improved DNA sequencing in the chain termination method or analysis of DNA fragments.

It is a particular object of the present invention to provide BODIPY® fluorophores for DNA sequencing wherein the BODIPY® fluorophore is attached to a nucleotide at a 3 BODIPY® position.

It is an object of the present invention to provide methods for the use of a class of dyes particularly suited for the chain termination method of DNA sequencing. It is also an object of the present invention to provide methods for labelling internally RNA or DNA fragments by enzymatic incorporation of dye-labeled ribonucleotides or deoxynucleotides. The labeled fragments may then be analyzed.

It is a further object of the present invention to provide methods for the use of BODIPY® fluorophores which have been modified so that a BODIPY® fluorophore can be used to replace a prior art fluorophore in DNA sequencing such that conventional software may be used. BODIPY® fluorophores can be used in one out of the four reactions, two out of the four reactions or three out of the four reactions.

If BODIPY® fluorophores are used in four out of the four reactions, a particular object of the present invention is to provide methods for the use of BODIPY® fluorophores for automated DNA sequencing which, since the particular BODIPY® fluorophores alter the mobility of the corresponding termination products in the same way, nullifies the need for chemical alteration of the fluorophore or software correction to generate evenly-spaced DNA sequences.

Thus, in accomplishing the foregoing objects, there is provided a method for analysis of DNA fragments wherein said DNA fragments are labeled with at least one BODIPY® fluorophore. In accomplishing the foregoing objects, there is provided in accordance with the present invention, a method for distinguishing polynucleotides having different 3'-terminal dideoxyribonucleotides in any method of chain termination DNA sequencing, the method comprising the steps of: forming a mixture of a first, a second, a third, and a fourth class of polynucleotides, each polynucleotide in the first class having a 3'-terminal dideoxyadenosine triphosphate, said 3'-terminal dideoxyadenosine triphosphate being attached at the 7 position of the 7-deazapurine to a 3-amino-1-propynyl linker, said linker then attached to a BODIPY® linker at a 3 position of a first BODIPY® fluorophore that contains at least one reactive functional group; each polynucleotide in the second class having a 3'-terminal dideoxycytidine triphosphate, said 3'-terminal dideoxycytidine triphosphate being attached at the 5 position of the pyrimidine to a 3-amino-1-propynyl linker, said linker then attached to a BODIPY® linker at a 3 position of a second BODIPY® fluorophore that contains at least one reactive functional group; each polynucleotide in the third class having a 3'-terminal dideoxyguanosine triphosphate, said 3'-terminal dideoxyguanosine triphosphate being attached at the 7 position of the 7-deazapurine to a 3-amino-1-propynyl linker, said linker then attached to a BODIPY® linker at a 3 position of a third BODIPY® fluorophore that contains at least one reactive functional group; each polynucleotide in the fourth class having a 3'-terminal dideoxythymidine triphosphate, said 3'-terminal dideoxythymidine triphosphate being attached at the 5 position of the pyrimidine to a 3-amino-1-propynyl linker, said linker then attached to a BODIPY® linker at a 3 position of a fourth BODIPY® fluorophore that contains at least one reactive functional group; wherein if said first, second, third and fourth BODIPY® fluorophores are all different, said polynucleotides can be electrophoresed in a same or a different lane; or wherein if any of said first, second, third or fourth fluorophores are the same, said polynucleotides labeled with said same fluorophores are electrophoresed in separate lanes; electrophoretically separating on a gel by size the polynucleotides; illuminating with an illumination beam the bands on the gel, the illumination beam being capable of causing the fluorophores to fluoresce; and identifying the classes of polynucleotides in the bands by the fluorescence or absorption spectrum of the fluorophores.

Further, in accomplishing the foregoing objects there is provided a method for distinguishing polynucleotides having different ribonucleotides in any method of labelling polynucleotides by enzymatic incorporation, the method comprising the steps of: forming a mixture of a first, a second, a third, and a fourth class of polynucleotides, each polynucleotide in the first class having an adenosine triphosphate, said adenosine triphosphate being attached at the 7 position of the 7-deazapurine to a 3-amino-1-propynyl linker, said linker then attached to a BODIPY® linker at a 3 position of a first BODIPY® fluorophore that contains at least one reactive functional group; each polynucleotide in the second class having a cytidine triphosphate, said cytidine triphosphate being attached at the 5 position of the pyrimidine to a 3-amino-1-propynyl linker, said linker then attached to a BODIPY® linker at a 3 position of a second BODIPY® fluorophore that contains at least one reactive functional group; each polynucleotide in the third class having a guanosine triphosphate, said guanosine triphosphate being attached at the 7 position of the 7-deazapurine to a 3-amino-1-propynyl linker, said linker then attached to a BODIPY® linker at a 3 position of a third BODIPY® fluorophore that contains at least one reactive functional group; each polynucleotide in the fourth class having a uracil, said uracil triphosphate being attached at the 5 position of the pyrimidine to a 3-amino-1-propynyl linker, said linker then attached to a BODIPY® linker at a 3 position of a fourth BODIPY® flourophore that contains at least one reactive functional group; wherein if said first, second, third and fourth BODIPY® fluorophores are all different, said polynucleotides can be electrophoresed in a same or a different lane; or wherein if any of said first, second, third or fourth fluorophores are the same, said polynucleotides labeled with said same fluorophores are electrophoresed in separate lanes; electrophoretically separating on a gel by size the polynucleotides; illuminating with an illumination beam the bands on the gel, the illumination beam being capable of causing the fluorophores to fluoresce; and identifying the classes of polynucleotides in the bands by the fluorescence or absorption spectrum of the fluorophores.

Additionally, in accomplishing the foregoing objects, there is provided a method for a method for distinguishing polynucleotides having different deoxyribonucleotides in any method of labelling polynucleotides by enzymatic incorporation, the method comprising the steps of: forming a mixture of a first, a second, a third, and a fourth class of polynucleotides, each polynucleotide in the first class having a deoxyadenosine triphosphate, said deoxyadenosine triphosphate being attached at the 7 position of the 7-deazapurine to a 3-amino-1-propynyl linker, said linker then attached to a BODIPY® linker at a 3 position of a first BODIPY® fluorophore that contains at least one reactive functional group; each polynucleotide in the second class having a deoxycytidine triphosphate, said deoxycytidine triphosphate being attached at the 5 position of the pyrimidine to a 3-amino-1-propynyl linker, said linker then attached to a BODIPY® linker at a 3 position of a second BODIPY® fluorophore that contains at least one reactive functional group; each polynucleotide in the third class having a deoxyguanosine triphosphate, said deoxyguanosine triphosphate being attached at the 7 position of the 7-deazapurine to a 3-amino-1-propynyl linker, said linker then attached to a BODIPY® linker at a 3 position of a third BODIPY® fluorophore that contains at least one reactive functional group; each polynucleotide in the fourth class having a deoxythymidine triphosphate, said deoxythymidine triphosphate being attached at the 5 position of the pyrimidine to a 3-amino-1-propynyl linker, said linker then attached to a BODIPY® linker at a 3 position of a fourth BODIPY® fluorophore that contains at least one reactive functional group; wherein if said first, second, third and fourth BODIPY® fluorophores are all different, said polynucleotides can be electrophoresed in a same or a different lane; or wherein if any of said first, second, third or fourth fluorophores are the same, said polynucleotides labeled with said same fluorophores are electrophoresed in separate lanes; electrophoretically separating on a gel by size the polynucleotides; illuminating with an illumination beam the bands on the gel, the illumination beam being capable of causing the fluorophores to fluoresce; and identifying the classes of polynucleotides in the bands by the fluorescence or absorption spectrum of the fluorophores.

Other and further objects, features and advantages will be apparent and the invention more readily understood from a reading of the following specification and by reference to the accompanying drawings forming a part thereof, wherein the examples of the presently preferred embodiments of the invention are given for the purposes of disclosure.

DESCRIPTION OF THE DRAWINGS

The drawings and figures are not to scale and certain features mentioned may be exaggerated in scale or shown in schematic form in the interest of clarity and conciseness.

DETAILED DESCRIPTION OF THE INVENTION

It will be apparent to one skilled in the art that various substitutions and modifications may be made to the invention disclosed herein without departing from the scope and the spirit of the invention.

As used herein, "BODIPY®" shall refer to a class of modified, spectrally-discriminating fluorophores wherein the parent heterocyclic molecule is a dipyrromethaneboron difluoride compound; specifically, various substituted 4,4-difluoro-4-bora-3a,4a-diaza-s-indacenes. The BODIPY® fluorophores of the present invention have a BODIPY linker at the 3 position of the BODIPY® molecule that contains at least one functional group capable of attachment to AP-3 ribonucleotides, AP-3 deoxyribonucleotides or AP-3 dideoxyribonucleotides.

Specific BODIPY® fluorophores useful in the present invention include BODIPY®s with adsorption maxima of about 450 to 700, and emission maxima of about 450 to 700. Preferred embodiments include BODIPY®s with adsorption maxima of about 480 to 650, and emission maxima of about 480 to 650. Examples of preferred embodiment BODIPY®s include BODIPY®503/512-SE (4,4-difluoro-5,7-dimethyl-4-bora-3a,4a-diaza-s-indacene-3-propionic acid), BODIPY® 523/547 (4,4-difluoro-5-phenyl-4-bora-3a,4a-diaza-s-indacene-3-propionic acid), BODIPY® 530/550 (4,4-difluoro-5,7-diphenyl-4-bora-3a,4a-diaza-s-indacene-3-propionic acid), BODIPY® 558/568 (4,4-difluoro-5-(2thienyl)-4-bora-3a,4a-diaza-s-indacene-3-propionic acid), BODIPY® 564/570 (4,4-difluoro-5-styryl-4-bora-3a,4a-diaza-s-indacene-3-propionic acid), BODIPY® 576/589 (4,4-difluoro-5-(2-pyrrolyl)-4-bora-3a,4a-diaza-s-indacene-3-propionic acid), BODIPY® 581/591 (4,4-difluoro-5-(4-phenyl-1,3-butadienyl)-4-bora-3a,4a-diaza-s-indacene-3-propionic acid), and BODIPY® 589/616 (6-(((4-(4,4-difluoro-5-(2-thienyl)-4-bora-3a,4a-diaza-s-indacene-3-yl) phenoxy)acetyl)amino)hexanoic acid). See FIG. 1.

Figure 2:
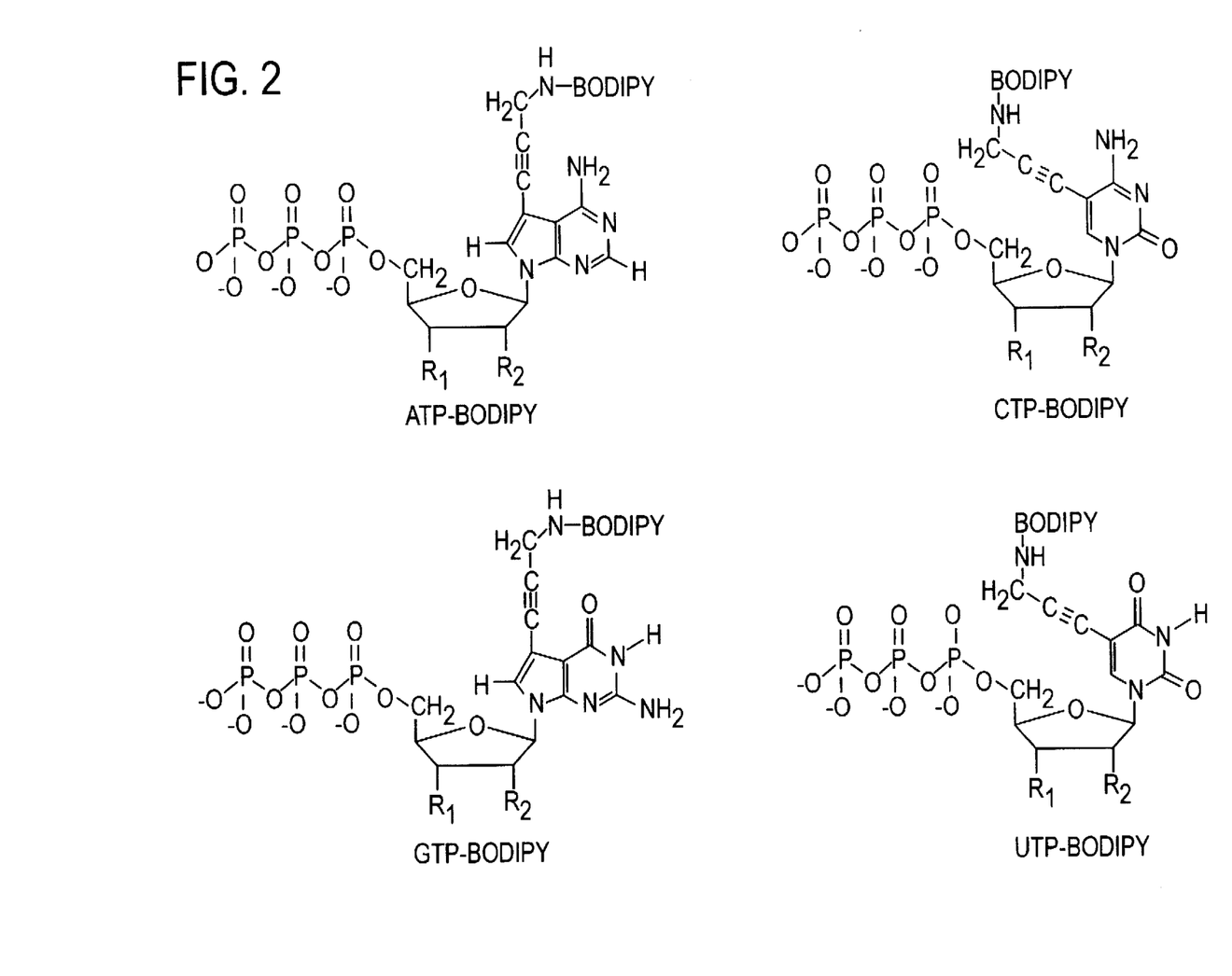
FIG. 2: Chemical structures of AP-3 nucleotides are shown, where $R_1$=OH and $R_2$=OH for ribonucleotides; $R_1$=OH and $R_2$=H for deoxynucleotides; and $R_1$=H and $R_2$=H for dideoxyribonucleotides.

As used herein, "AP-3" or "AP-3 nucleotide" refers to the 3-amino-1-propynyl linker attached to the 5 position of pyrimidines or the 7 position of 7-deazapurines. See FIG. 2.

Figure 1:
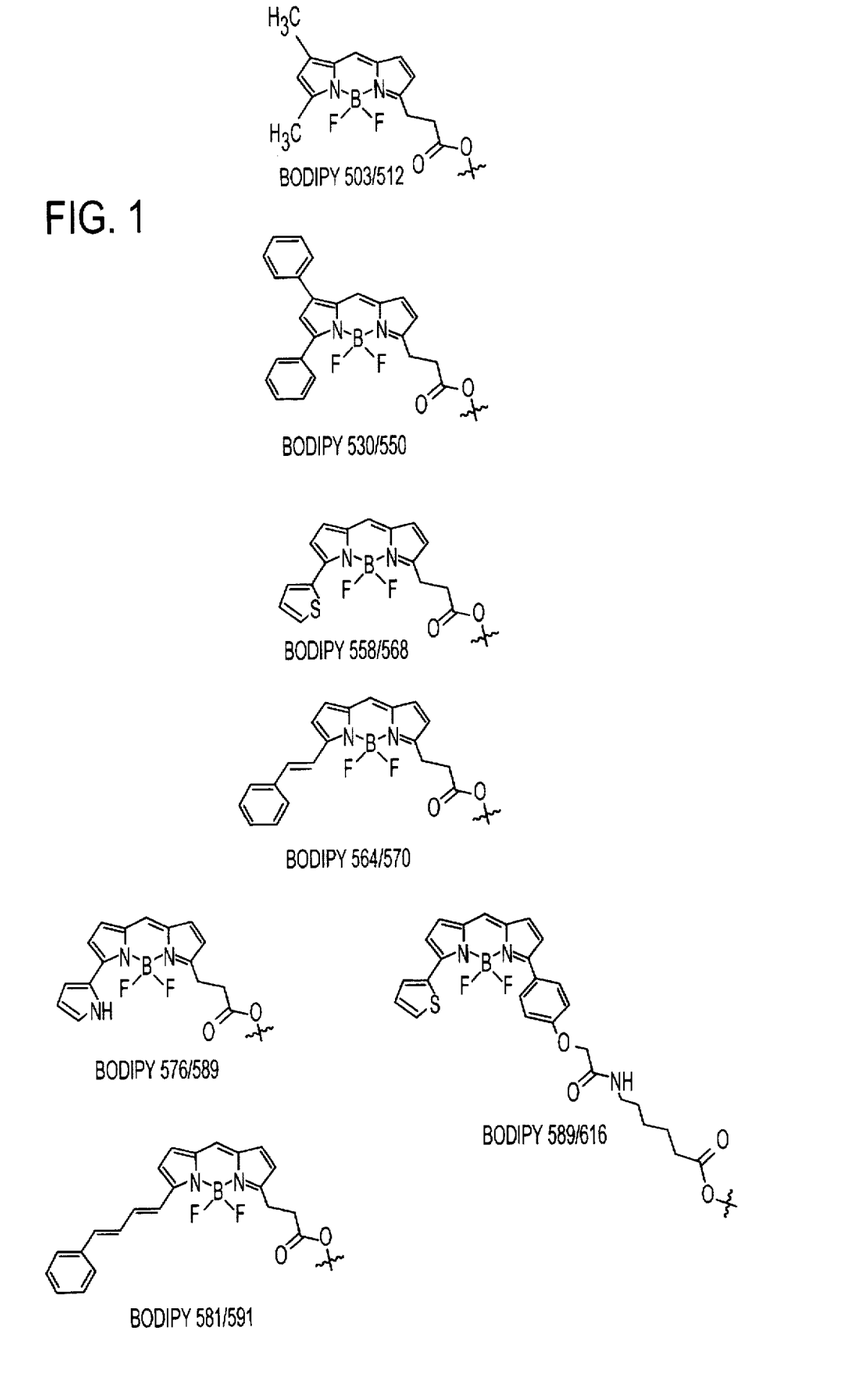
FIG. 1: Chemical structures of several different substituted BODIPY® fluorophores (4,4-difluoro-4-bora-3a,4a-diaza-s-indacene) used in the present invention are shown.

As used herein, "BODIPY® linker" or "BODIPY® functional group" refers to a substituted or unsubstituted alkyl containing one to thirty carbons and at least one functional group. Two different BODIPY® linkers are illustrated in FIG. 1.

As used herein, "DNA sequencing" refers to the process of determining the nucleic acid sequence of a DNA strand of interest.

As used herein "automated DNA sequencing" refers to determining the sequence of a DNA strand of interest using an apparatus comprising an area having an electrophoresis gel, means for introducing labeled DNA fragments to the gel area, and photometric means for monitoring said labeled DNA fragments as they move through the gel. "Automated DNA sequencer" refers to the instrument which is able to perform automated DNA sequencing.

As used herein, "automated GeneScanner" refers to an instrument capable of performing analysis of fluorescently-labeled DNA or RNA.

As used herein, "sequencing primer" means a synthetic oligonucleotide, restriction fragment, enzymatically-synthesized DNA fragment, or the like which hybridizes specifically to a region proximate to the region of DNA to be sequenced. "Universal sequencing primer" refers to commonly-used primers known in the art, generally one that hybridizes specifically to a region of the M13 vector near the 3' end of the cloned insert. Specific examples of universal sequencing primers known in the art are –21M13, –M13–40 and –36M13.

As used herein, electrophoresis "lanes", "tracks" or "columns" refers to the particular path in the electrophoretic medium in which the sequencing products are run. For example, the sequencing products terminating in dideoxyadenosine triphosphate, dideoxycytodine, dideoxyguanosine triphosphate or dideoxythymidine triphosphate may be run in four separate lanes, or, if labeled differentially, in the same lane.

One novel aspect of the present invention is to provide a method for distinguishing polynucleotides having different 3'-terminal dideoxyribonucleotides in any method of chain termination DNA sequencing, the method comprising the steps of: forming a mixture of a first, a second, a third, and a fourth class of polynucleotides, each polynucleotide in the first class having a 3'-terminal dideoxyadenosine triphosphate, said 3'-terminal dideoxyadenosine triphosphate being attached at the 7 position of the 7-deazapurine to a 3-amino-1-propynyl linker, said linker then attached to a BODIPY® linker at a 3 position of a first BODIPY® fluorophore that contains at least one reactive functional group; each polynucleotide in the second class having a 3' terminal dideoxycytidine triphosphate, said 3'-terminal dideoxycytidine triphosphate being attached at the 5 position of the pyrimidine to a 3-amino-1-propynyl linker, said linker then attached to a BODIPY® linker at a 3 position of a second BODIPY® fluorophore that contains at least one reactive functional group; each polynucleotide in the third class having a 3'-terminal dideoxyguanosine triphosphate, said 3'-terminal dideoxyguanosine triphosphate being attached at the 7 position of the 7-deazapurine to a 3-amino-1-propynyl linker, said linker then attached to a BODIPY® linker at a 3 position of a third BODIPY® fluorophore that contains at least one reactive functional group; each polynucleotide in the fourth class having a 3'-terminal dideoxythymidine triphosphate, said 3'-terminal dideoxythymidine triphosphate being attached at the 5 position of the pyrimidine to a 3-amino-3-propynyl linker, said linker then attached to a BODIPY® linker at a 3 position of a fourth BODIPY® fluorophore that contains at least one reactive functional group; wherein if said first, second, third and fourth BODIPY® fluorophores are all different, said polynucleotides can be electrophoresed in a same or a different lane; or wherein if any of said first, second, third or fourth fluorophores are the same, said polynucleotides labeled with said same fluorophores are electrophoresed in separate lanes; electrophoretically separating on a gel by size the polynucleotides; illuminating with an illumination beam the bands on the gel, the illumination beam being capable of causing the fluorophores to fluoresce; and identifying the classes of polynucleotides in the bands by the fluorescence or absorption spectrum of the fluorophores.

Yet another embodiment of the present invention provides for the method of distinguishing polynucleotides having different ribonucleotides in any method of labelling polynucleotides by enzymatic incorporation, the method comprising the steps of: forming a mixture of a first, a second, a third, and a fourth class of polynucleotides, each polynucleotide in the first class having an adenosine triphosphate, said adenosine triphosphate being attached at the 7 position of the 7-deazapurine to a 3-amino-1-propynyl linker, said linker then attached to a BODIPY® linker at a 3 position of a first BODIPY® fluorophore that contains at least one reactive functional group; each polynucleotide in the second class having a cytidine triphosphate, said cytidine triphosphate being attached at the 5 position of the pyrimidine to a 3-amino-3-propynyl linker, said linker then attached to a BODIPY® linker at a 3 position of a second BODIPY® fluorophore that contains at least one reactive functional group; each polynucleotide in the third class having a guanosine triphosphate, said guanosine triphosphate being attached at the 7 position of the 7-deazapurine to a 3-amino-1-propynyl linker, said linker then attached to a BODIPY® linker at a 3 position of a third BODIPY® fluorophore that contains at least one reactive functional group; each polynucleotide in the fourth class having a uracil triphosphate, said uracil triphosphate being attached at the 5 position of the pyrimidine to a 3-amino-3-propynyl linker, said linker then attached to a BODIPY® linker at a 3 position of a fourth BODIPY® fluorophore that contains at least one reactive functional group; wherein if said first, second, third and fourth BODIPY® fluorophores are all different, said polynucleotides can be electrophoresed in a same or a different lane; or wherein if any of said first, second, third or fourth fluorophores are the same, said polynucleotides labeled with said same fluorophores are electrophoresed in separate lanes; electrophoretically separating on a gel by size the polynucleotides; illuminating with an illumination beam the bands on the gel, the illumination beam being capable of causing the fluorophores to fluoresce; and identifying the classes of polynucleotides in the bands by the fluorescence or absorption spectrum of the fluorophores.

In another embodiment of the present invention, there is provided a method for distinguishing polynucleotides having different deoxyribonucleotides in any method of labelling polynucleotides by enzymatic incorporation, the method comprising the steps of: forming a mixture of a first, a second, a third, and a fourth class of polynucleotides, each polynucleotide in the first class having a deoxyadenosine triphosphate, said deoxyadenosine triphosphate being attached at the 7 position of the 7-deazapurine to a 3-amino-1-propynyl linker, said linker then attached to a BODIPY® linker at a 3 position of a first BODIPY® fluorophore that contains at least one reactive functional group; each polynucleotide in the second class having a deoxycytidine triphosphate, said deoxycytidine triphosphate being attached at the 5 position of the pyrimidine to a 3-amino-1-propynyl linker, said linker then attached to a BODIPY® linker at a 3 position of a second BODIPY® fluorophore that contains at least one reactive functional group; each polynucleotide in the third class having a deoxyguanosine triphosphate, said deoxyguanosine triphosphate being attached at the 7 position of the 7-deazapurine to a 3-amino-3-propynyl linker, said linker then attached to a BODIPY® linker at a 3 position of a third BODIPY® fluorophore that contains at least one reactive functional group; each polynucleotide in the fourth class having a deoxythymidine triphosphate, said deoxythymidine triphosphate being attached at the 5 position of the pyrimidine to a 3-amino-1-propynyl linker, said linker then attached to a BODIPY® linker at a 3 position of a fourth BODIPY® fluorophore that contains at least one reactive functional group; wherein if said first, second, third and fourth BODIPY® fluorophores are all different, said polynucleotides can be electrophoresed in a same or a different lane; or wherein if any of said first, second, third or fourth fluorophores are the same, said polynucleotides labeled with said same fluorophores are electrophoresed in separate lanes; electrophoretically separating on a gel by size the polynucleotides; illuminating with an illumination beam the bands on the gel, the illumination beam being capable of causing the fluorophores to fluoresce; and identifying the classes of polynucleotides in the bands by the fluorescence or absorption spectrum of the fluorophores.

Another aspect of the present invention allows BODIPY® fluorophores to be used in combination with prior art fluorophores and commercially-available software.

In a preferred embodiment, said BODIPY® fluorophores have an adsorption maxima of about 450 to 700, and an emission maxima of about 450 to 700.

In yet another preferred embodiment, the BODIPY® fluorophores are selected from the group of BODIPY® 530/550; BODIPY® 503/512; BODIPY® 564/570; BODIPY® 589/616; BODIPY® 581/591; BODIPY® 523/547; BODIPY® 558/568; and BODIPY® 576/589. The structure of these BODIPY® dyes are shown in FIG. 1.

In one aspect of the present invention, said adenosine triphosphate, dexoyadenosine triphosphate or 3'-terminal dideoxyadenosine triphosphate is labeled with BODIPY® 523/547 or BODIPY® 530/550; said cytidine triphosphate, deoxycytidine triphosphate or 3'-terminal dideoxycytidine triphosphate is labeled with BODIPY® 576/589, BODIPY® 581/591, or BODIPY® 589/616; said guanosine triphosphate, deoxyguanosine triphosphate or 3'-terminal dideoxyguanosine triphosphate is labeled with BODIPY® 503/512; and said uracil triphosphate, deoxythymidine triphosphate or 3'-terminal dideoxythymidine triphosphate is labeled with BODIPY® 558/568 or BODIPY® 564/570. Labelling the polynucleotides in this manner allows for the use of conventional, commercially-available software. However, it should be clear that one skilled in the art of computer software design that software could be altered such that the software could read different BODIPY® dyes attached to different classes of polynucleotides.

In a preferred embodiment, said chain termination method of DNA sequencing is performed by an automated DNA sequencing instrument.

In another preferred embodiment, said internal labelling is performed by an automated GeneScanner.

In an additional preferred embodiment, the method of the present invention further includes the step of extending from a primer a plurality of deoxynucleotides by means of a DNA polymerase suitable for DNA sequencing or a reverse transcriptase suitable for DNA sequencing in the presence of dideoxyadenosine triphosphate, dideoxycytosine triphosphate, dideoxyguanosine triphosphate, and dideoxythymidine triphosphate to form said first, second, third, and fourth classes of polynucleotides.

In another preferred embodiment of the present invention, said DNA polymerase is selected from the group of Klenow fragment, Sequenase®, Bst DNA polymerase, AmpliTaq® DNA polymerase, Pfu (exo-)DNA polymerase, Thermosequenase®, rTth DNA polymerase or Vent(exo-)® DNA polymerase, and said reverse transcriptase is selected from the group of AMV-RT or M-MuLV-RT.

In the case of RNA, RNA polymerase is used.

The following example is offered by way of illustration and is not intended to limit the invention in any manner. The example shows the procedures for labelling AP-3 nucleotides.

One skilled in the art will appreciate readily that the present invention is well adapted to carry out the objects and obtain the ends and advantages mentioned, as well as those inherent therein. The oligonucleotides, dyes, methods, procedures and techniques described herein are presently representative of the preferred embodiments, are intended to be exemplary, and are not intended as limitations on the scope of the invention. Changes therein and other uses will occur to those skilled in the art, and are encompassed within the spirit of the invention or defined by the scope of the appended claims. All references specifically cited herein are incorporated by reference.

EXAMPLE

Method for labelling AP-3 nucleotides

A. Reagents: AP-3 nucleotides were purchased from DuPont NEN Products and dissolved and diluted to a final concentration of 10 mM. All BODIPY®-SE dyes were purchased from Molecular Probes and were resuspended in anhydrous DMSO (50 mg/mL).

B. Fluorescent terminators: To AP-3 ribonucleotides, deoxyribonucleotides or dideoxynucleotides (0.1 µmole), 30 µL of 0.25M NaHCO$_3$Na$_2$CO$_3$, pH 9.0 buffer was added followed by the addition of 5 µL of BODIPY-SE dyes. All dye labelling reactions were incubated at 25° C. for 16 h. Dye-labeled nucleotides were purified by RP-HPLC, evaporated to near dryness and diluted in 10 mM Tris-HCl, pH 8.0, 1 mM EDTA.

C. RP-HPLC: The RP-HPLC hardware system consisted of a Beckman model 127 gradient solvent module, A Rheodyne model 7125 injector, an Applied Biosystems (ABI) model 759A absorbance detector, and a Spectra-Physics model SP4600 DataJet integrator. Gradient RP-HPLC was performed using an ABI aquapore OD-300 column (4.6 mm×250 mm) where "Buffer A" is 100 mM triethylammonium acetate (TEAA), pH 7.0 and "Buffer B" is 100 mM TEAA, 70% (v/V) acetonitrile. Dye-labeled ribonucleotides, deoxynucleotides or dideoxynucleotides were purified using the following gradient conditions: 0% B, 5 minutes; 0% B–40% B, 30 minutes; 40% B–100% B, 18 minutes: 5 minutes at a flow rate of 1.0 mL per minute.

We claim:

1. A method for distinguishing polynucleotides having different 3'-terminal dideoxynucleotides in any method of chain termination DNA sequencing, said method comprising the steps of:

forming a mixture of a first, a second, a third, and a fourth class of polynucleotides, each polynucleotide in the first class having a 3'-terminal dideoxyadenosine triphosphate, said 3'-terminal dideoxyadenosine triphosphate being attached at the 7 position of the 7-deazapurine to a 3-amino-1-propynyl linker, said linker then attached to a BODIPY® dipyrromethenoboron difluoride linker at a 3 position of a first BODIPY® fluorophore that contains at least one reactive functional group; each polynucleotide in the second class having a 3'-terminal dideoxycytidine triphosphate, said 3'-terminal dideoxycytidine triphosphate being attached at the 5 position of the pyrimidine to a 3-amino-1-propynyl linker, said linker then attached to a BODIPY® linker at a 3 position of a second BODIPY® fluorophore that contains at least one reactive functional group; each polynucleotide in the third class having a 3'-terminal dideoxyguanosine triphosphate, said 3'-terminal dideoxyguanosine triphosphate being attached at the 7 position of the 7-deazapurine to a 3-amino-1-propynyl linker, said linker then attached to a BODIPY® linker at a 3 position of a third BODIPY® fluorophore that contains at least one reactive functional group; each polynucleotide in the fourth class having a 3'-terminal dideoxythymidine triphosphate, said 3'-terminal dideoxythymidine triphosphate being attached at the 5 position of the pyrimidine to a 3-amino-1-propynyl linker, said linker then attached to a BODIPY® linker at a 3 position of a fourth BODIPY® fluorophore that contains at least one reactive functional group; wherein if said first, second, third and fourth BODIPY® fluorophores are all different, said polynucleotides can be electrophoresed in a same or a different lane; or wherein if any of said first, second, third or fourth fluorophores are the same, said polynucleotides labeled with said same fluorophores are electrophoresed in separate lanes;

electrophoretically separating on a gel by size the polynucleotides so as to produce bands on the gel;

illuminating with an illumination beam the bands on the gel, the illumination beam being capable of causing the fluorophores to fluoresce; and identifying the classes of polynucleotides in the bands by the fluorescence or absorption spectrum of the fluorophores.

2. The method of claim 1, wherein the BODIPY® fluorophores are selected from the group of BODIPY® 530/550; BODIPY® 503/512; BODIPY® 564/570; BODIPY® 589/616; BODIPY® 581/591; BODIPY® 523/547; BODIPY® 558/568; and BODIPY® 576/589.

3. The method of claim 1, wherein said 3'-terminal dideoxyadenosine triphosphate is labeled with BODIPY® 523/547 or BODIPY® 530/550; said 3'-terminal dideoxycytidine triphosphate is labeled with BODIPY® 576/589, BODIPY® 581/591, or BODIPY® 589/616; said 3'-terminal dideoxyguanosine triphosphate is labeled with BODIPY® 503/512; and said 3'-terminal dideoxythymidine triphosphate is labeled with BODIPY® 558/568 or BODIPY® 564/570.

4. The method of claim 1, wherein said BODIPY® fluorophores have an adsorption maxima of about 450 to 700, and an emission maxima of about 450 to 700.

5. The method of claim 1, wherein said chain termination method of DNA sequencing is performed by an automated DNA sequencing instrument.

6. The method of claim 1, wherein said classes of polynucleotides are formed using a DNA polymerase selected from the group of Klenow fragment, Sequenase®, Bst DNA polymerase, AmpliTaq® DNA polymerase, Pfu(exo-)DNA polymerase, Thermosequenase®, rTth DNA polymerase or Vent(exo-) DNA polymerase, and the reverse transcriptase is selected from the group of AMV-RT or M-MuLV-RT.

7. A method for distinguishing polynucleotides having different ribonucleotides in any method of labelling polynucleotides by enzymatic incorporation, said method comprising the steps of:

forming a mixture of a first, a second, a third, and a fourth class of polynucleotides, each polynucleotide in the first class having an adenosine triphosphate, said adenosine triphosphate being attached at the 7 position of the 7-deazapurine to a 3-amino-1-propynyl linker, said linker then attached to a BODIPY® linker at a 3 position of a first BODIPY® fluorophore that contains at least one reactive functional group; each polynucleotide in the second class having a cytidine triphosphate, said cytidine triphosphate being attached at the 5 position of the pyrimidine to a 3-amino-1-propynyl linker, said linker then attached to a BODIPY® linker at a 3 position of a second BODIPY® fluorophore that contains at least one reactive functional group; each polynucleotide in the third class having a guanosine triphosphate, said guanosine triphosphate being attached at the 7 position of the 7-deazapurine to a 3-amino-1-propynyl linker, said linker then attached to a BODIPY® linker at a 3 position of a third BODIPY® fluorophore that contains at least one reactive functional group; each polynucleotide in the fourth class having a uracil triphosphate, said uracil triphosphate being attached at the 5 position of the pyrimidine to a 3-amino-1-propynyl linker, said linker then attached to a BODIPY® linker at a 3 position of a fourth BODIPY® fluorophore that contains at least one reactive functional group; wherein if said first, second, third and fourth BODIPY® fluorophores are all different, said polynucleotides can be electrophoresed in a same or a different lane; or wherein if any of said first, second, third or fourth fluorophores are the same, said polynucleotides labeled with said same fluorophores are electrophoresed in separate lanes;

electrophoretically separating on a gel by size the polynucleotides;

illuminating with an illumination beam the bands on the gel, the illumination beam being capable of causing the fluorophores to fluoresce; and identifying the classes of polynucleotides in the bands by the fluorescence or absorption spectrum of the fluorophores.

8. The method of claim 7, wherein the BODIPY® fluorophores are selected from the group of BODIPY® 530/550; BODIPY® 503/512; BODIPY® 564/570; BODIPY® 589/616; BODIPY® 581/591; BODIPY® 523/547; BODIPY® 558/568; and BODIPY® 576/589.

9. The method of claim 7, wherein said adenosine triphosphate is labeled with BODIPY® 523/547 or BODIPY® 530/550; said cytidine triphosphate is labeled with BODIPY® 576/589, BODIPY® 581/591, or BODIPY® 589/616; said guanosine triphosphate is labeled with BODIPY® 503/512; and said uracil triphosphate is labeled with BODIPY® 558/568 or BODIPY® 564/570.

10. The method of claim 7, wherein said BODIPY® fluorophores have an adsorption maxima of about 450 to 700, and an emission maxima of about 450 to 700.

11. The method of claim 7, wherein said internal labelling and distinguishing polynucleotides is performed by an automated GeneScanner.

12. A method for distinguishing polynucleotides having different deoxyribonucleotides in any method of labelling polynucleotides by enzymatic incorporation, said method comprising the steps of:

forming a mixture of a first, a second, a third, and a fourth class of polynucleotides, each polynucleotide in the first class having a deoxyadenosine triphosphate, said deoxyadenosine triphosphate being attached at the 7 position of the 7-deazapurine to a 3-amino-3-propynyl linker, said linker then attached to a BODIPY® linker at a 3 position of a first BODIPY® fluorophore that contains at least one reactive functional group; each polynucleotide in the second class having a deoxycytidine triphosphate, said deoxycytidine triphosphate being attached at the 5 position of the pyrimidine to a 3-amino-1-propynyl linker, said linker then attached to a BODIPY® linker at a 3 position of a second BODIPY® fluorophore that contains at least one reactive functional group; each polynucleotide in the third class having a deoxyguanosine triphosphate, said deoxyguanosine triphosphate being attached at the 7 position of the 7-deazapurine to a 3-amino-3-propynyl linker, said linker then attached to a BODIPY® linker at a 3 position of a third BODIPY® fluorophore that contains at least one reactive functional group; each polynucleotide in the fourth class having a deoxythymidine triphosphate, said deoxythymidine triphosphate being attached at the 5 position of the pyrimidine to a 3-amino-1-propynyl linker, said linker then attached to a BODIPY® linker at a 3 position of a fourth BODIPY® fluorophore that contains at least one reactive functional group; wherein if said first, second, third and fourth BODIPY® fluorophores are all different, said polynucleotides can be electrophoresed in a same or a different lane; or wherein if any of said first, second, third or fourth fluorophores are the same, said polynucleotides labeled with said same fluorophores are electrophoresed in separate lanes;

electrophoretically separating on a gel by size the polynucleotides;

illuminating with an illumination beam the bands on the gel, the illumination beam being capable of causing the fluorophores to fluoresce; and identifying the classes of polynucleotides in the bands by the fluorescence or absorption spectrum of the fluorophores.

13. The method of claim 12, wherein the BODIPY® fluorophores are selected from the group of BODIPY® 530/550; BODIPY® 503/512; BODIPY® 564/570; BODIPY® 589/616; BODIPY® 581/591; BODIPY® 523/547; BODIPY® 558/568; and BODIPY® 576/589.

14. The method of claim 12, wherein said deoxyadenosine triphosphate is labeled with BODIPY® 523/547 or BODIPY® 530/550; said deoxycytidine triphosphate is labeled with BODIPY® 576/589, BODIPY® 581/591, or BODIPY® 589/616; said deoxyguanosine triphosphate is labeled with BODIPY® 503/512; and said deoxythymidine triphosphate is labeled with BODIPY® 558/568 or BODIPY® 564/570.

15. The method of claim 12, wherein said BODIPY® fluorophores have an adsorption maxima of about 450 to 700, and an emission maxima of about 450 to 700.

16. The method of claim 12, wherein said internal labelling and distinguishing polynucleotides is performed by an automated GeneScanner.

17. The method of claim 12, wherein said classes of polynucleotides are formed using a DNA polymerase selected from the group of Klenow fragment, Sequenase®, Bst DNA polymerase, AmpliTaq® DNA polymerase, Pfu (exo-)DNA polymerase, Thermosequenase®, rTth DNA polymerase or Vent(exo-) DNA polymerase, and the reverse transcriptase is selected from the group of AMV-RT or M-MuLV-RT.

* * * * *